United States Patent [19]
Duvick et al.

[11] Patent Number: 5,905,187
[45] Date of Patent: May 18, 1999

[54] ANTIMICROBIAL PEPTIDES AND PLANT DISEASE RESISTANCE BASED THEREON

[75] Inventors: Jonathan P. Duvick; Tracy A. Rood; Aragula G. Rao, all of Polk County, Iowa

[73] Assignee: Pioneer Hi-Bred International, Inc., Des Moines, Iowa

[21] Appl. No.: 08/822,561

[22] Filed: Mar. 19, 1997

Related U.S. Application Data

[63] Continuation of application No. 08/442,910, May 17, 1995, abandoned, which is a continuation of application No. 07/536,127, Jun. 5, 1990, abandoned.

[51] Int. Cl.$^6$ ....................................................... C07K 1/14
[52] U.S. Cl. ........................................... 800/205; 530/300
[58] Field of Search ........................... 800/205, DIG. 52, 800/DIG. 56, DIG. 57, DIG. 58, DIG. 55, DIG. 9, DIG. 14; 536/23.1, 23.6, 24.3; 530/300; 435/172.3, 69.1

[56] References Cited

PUBLICATIONS

Bass et al. A maize ribosome–inactivating protein is controlled by the transcriptional activator Opaque–2. The Plant Cell. vol. 4, pp. 225–234, 1992.

*Primary Examiner*—Douglas W. Robinson
*Assistant Examiner*—Melissa L. Kimball

[57] ABSTRACT

CMIII, a small, basic maize seed peptide has been found to have antimicrobial properties. In a preferred embodiment, plant resistance to diseases caused by plant pathogens which are susceptible to CMIII is produced by inserting into the cells of a plant a gene whose expression causes production CMIII in antimicrobial amounts.

1 Claim, 8 Drawing Sheets

ANTIMICROBIAL PEPTIDES AND PLANT DISEASE RESISTANCE BASED THEREON

REFERENCE TO RELATED APPLICATIONS

This is a continuation application of prior application Ser. No. 08/442,910 filed May 17, 1995, now abandoned, which is a continuation application of prior application Ser. No. 07/536,127, filed Jun. 5, 1990, now abandoned.

TECHNICAL FIELD

This invention relates to materials and methods for killing fungi and other microorganisms which are harmful to plants, and materials and methods for imparting disease resistance to plants.

BACKGROUND OF THE INVENTION

Numerous fungi and bacteria are serious pests of common agricultural crops. One method of controlling diseases has been to apply antimicrobial organic or semiorganic chemicals to crops. This method has numerous, art-recognized problems. A more recent method of control of microorganism pests has been the use of biological control organisms which are typically natural competitors or inhibitors of the troublesome microorganisms. However, it is difficult to apply biological control organisms to large areas, and even more difficult to cause those living organisms to remain in the treated area for an extended period. Still more recently, techniques in recombinant DNA have provided the opportunity to insert into plant cells cloned genes which express antimicrobial compounds. This technology has given rise to additional concerns about eventual microbial resistance to well-known, naturally occurring antimicrobials, particularly in the face of heavy selection pressure, which may occur in some areas. Thus, a continuing need exists to identify naturally occurring antimicrobial compounds which can be formed by plant cells directly by translation of a single structural gene.

European Patent Application 204,590, based upon U.S. patent application Ser. No. 725,368, describes a method of genetically modifying a plant cell to control expression of heterologous foreign structure genes. In the method, the plant cell is transformed to contain a pRi T-DNA promoter and a heterologous foreign structural gene, the promoter and the structural gene being in such position and orientation with respect to one another that the structural gene is expressible in a plant cell under control of the promoter.

Likewise, European Patent Application 186,425, based upon U.S. patent application Ser. No. 685,824, describes a recombinant DNA expression vector which comprises (a) a transcription unit, flanked by T-DNA border sequences, which comprises a promoter and associated amino terminal region encoding sequences and a terminator signal sequence in which the sequences are derived from one or more genes which are naturally expressed in a plant cell, and (b) an antibiotic resistance gene-encoding sequence located between the promoter and associated amino-terminal region-encoding sequence and the terminator sequence and (c) a DNA fragment containing a replicon that is functional in Agrobacterium.

PCT application 8807087, based upon U.S. patent application Ser. No. 168,109, discloses a recombinant virus expression system comprising a Heliothis polyhedrin promoter and a nucleotide sequence encoding a heterologous peptide or protein, which may have antimicrobial activity.

BRIEF DESCRIPTION OF THE DRAWINGS

FIG. 6 is a plasmid map of plasmid pPHI414.

DISCLOSURE OF THE INVENTION

It has now been determined that a small, basic maize seed peptide, CMIII, has potent antimicrobial activity against common plant pathogens. CMIII is particularly active against the plant pathogenic fungus Sclerotinia, and also against the maize seed pathogen, *Fusarium graminearum*.

Thus, this invention provides a method for killing plant pathogens comprising introducing into the environment of the organisms an antimicrobial amount of a CMIII. The CMIII can be effectively applied to plants infested with the microorganisms by spray, dust or other formulation common to the antimicrobial arts. Alternatively, the CMIII can be incorporated into the tissues of a susceptible plant so that in the course of infesting the plant the pathogens will be exposed to antimicrobial amounts of CMIII. One method of doing this is to incorporate the CMIII in a non-phytotoxic vehicle which is adapted for systemic administration to the susceptible plants. This method is commonly employed with insecticidal materials which are designed to attack chewing insects and is well within the purview of one of ordinary skill in the art of insecticide and larvicide formulation. However, since the genes which code for CMIII can be isolated, cloned, inserted into an appropriate expression cassette, and introduced into cells of a susceptible plant species, an especially preferred embodiment of this method involves inserting into the genome of the plant a DNA sequence coding for CMIII in proper reading frame, together with transcription initiator and promoter sequences active in the plant. Transcription and translation of the DNA sequence under control of the regulatory sequences causes expression of the CMIII protein sequence at levels which provide an antimicrobial amount of the CMIII in the tissues of the plant which are normally infected by the pathogens.

The plant is preferably a plant susceptible to infection and damage by one or more of *Fusarium graminearum, Fusarium moniliforme, Aspergillus flavus, Alternaria longipes, Sclerotinia sclerotiorum,* and *Sclerotinia trifoliorum*. These include corn (*Zea mays*) and sorghum (*Sorghum bicolor*). However, this is not to be construed as limiting, inasmuch as these species are among the most difficult commercial crops to reliably transform and regenerate, and these microorganisms also infect certain other crops. Thus the methods of this invention are readily applicable via conventional techniques to numerous plant species, if they are found to be susceptible to the plant pests listed hereinabove, including, without limitation, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersionn, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura.

Preferred plants that are to be transformed according to the methods of this invention are cereal crops, including maize, rye, barley, wheat, sorghum, oats, millet, rice, triticale, sunflower, alfalfa, rape seed and soybean.

The DNA sequence which when expressed imparts antimicrobial activity is a structural gene which codes for CMIII as described herein. In general, since the object of the invention is to confer resistance to a microorganism to which the plant is susceptible, in some cases CMIII will not be native to the plant, i.e., the CMIII gene will come from a species other than the plant being transformed. However, in species which produce CMIII but in lower than antimicrobial amounts, it may be preferable to insert a gene for CMIII under strong constitutive promoter control to cause overproduction of CMIII, thus achieving antimicrobial levels and conferring effective disease resistance. Alternatively, where a plant produces CMIII but the CMIII is not produced in or not distributed to tissues which are normally affected by the disease, a tissue specific promoter can be used to provide localized expression or overproduction of CMIII. A tissue specific promoter can be used in any instance where it may be desirable to localize production of CMIII to an infected tissue or to a tissue which is efficient in production of CMIII.

The DNA sequences which code for CMIII in the practice of this invention can be obtained by conventional techniques and the gene can then be removed by use of appropriate restriction enzymes and spliced into a selected plant expression cassette. Alternatively, purified CMIII can be sequenced in its entirety using known methods, and synthetic DNA sequences can then be prepared which code for the appropriate sequence of amino acids, and this synthetic sequence can be inserted into an appropriate plant expression cassette.

Figure 4:
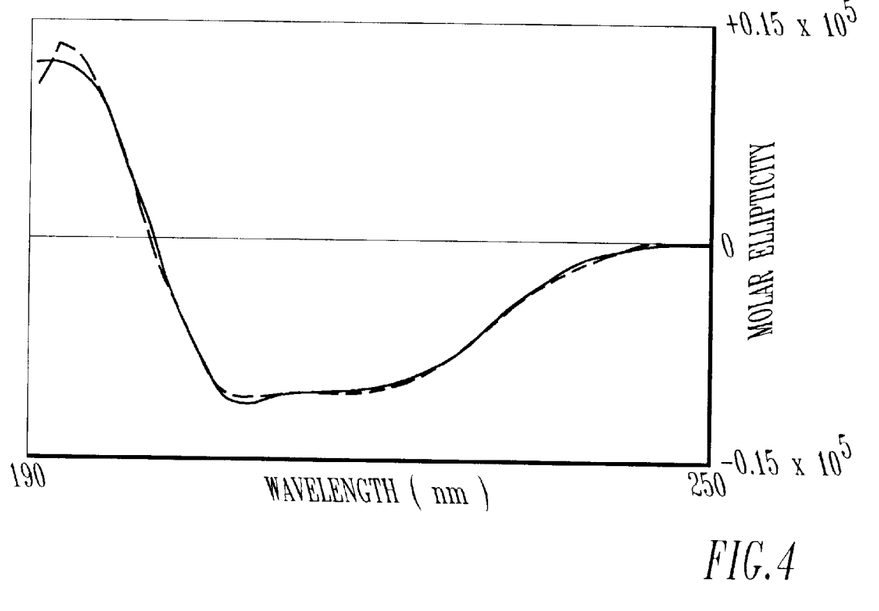
FIGS. 4, 5 & 6 illustrate the CD, absorption and flourescence spectra, respectively, of CM-III.
Figure 5:
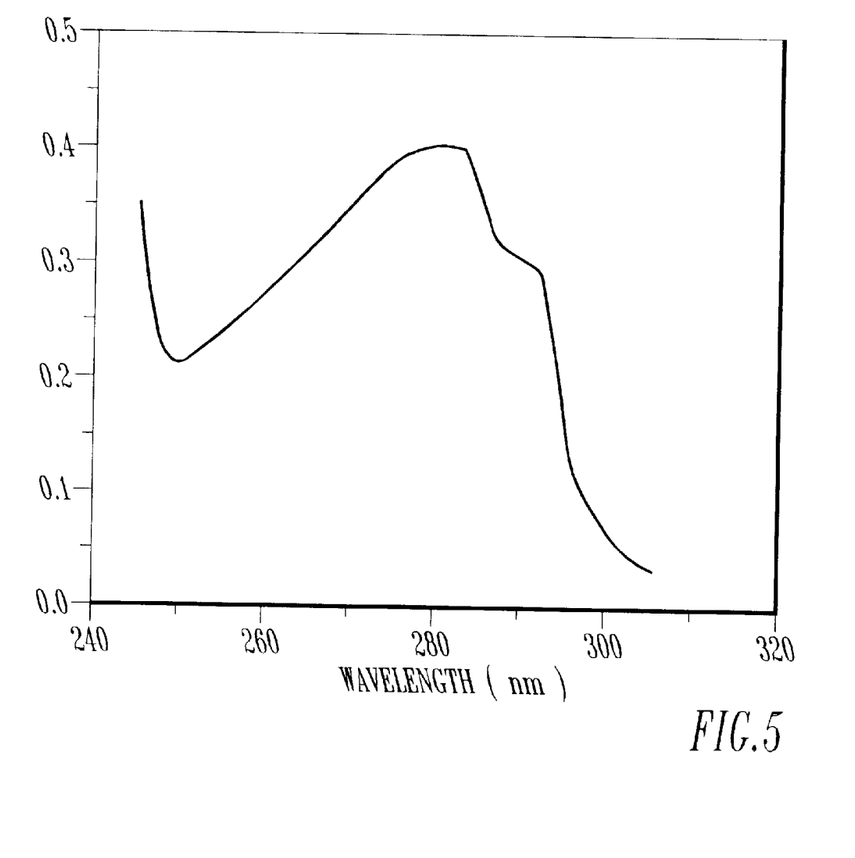
Figure 6:
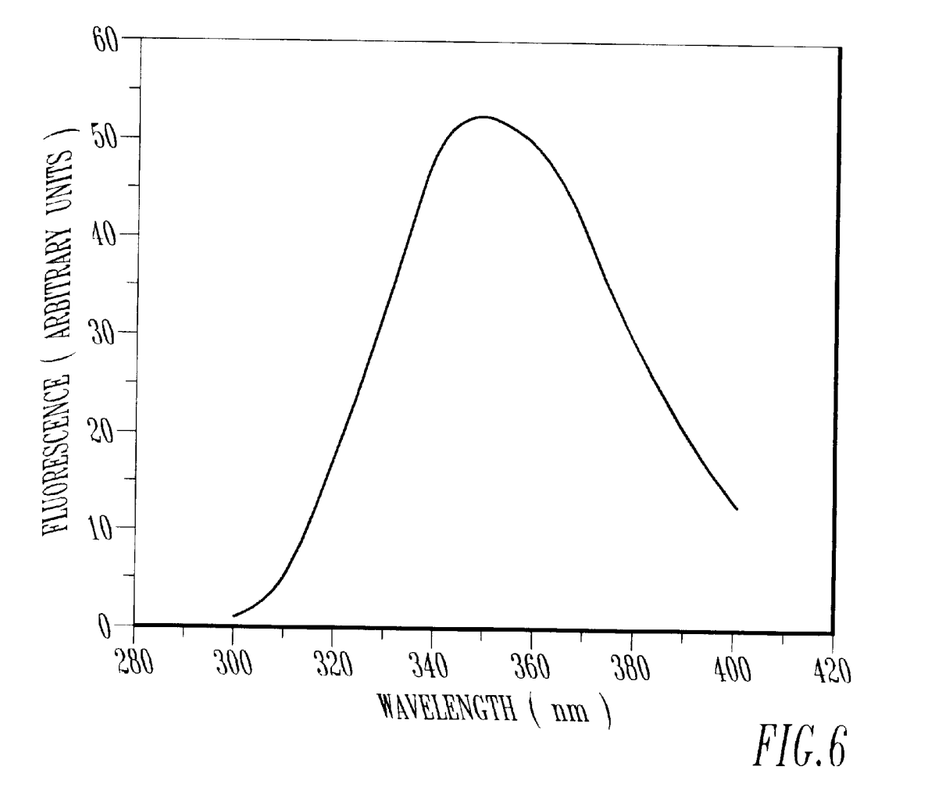

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic and cDNA encoding the gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a first genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs and CaMV promoters.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.,* 1:483–498 (1982)), and the promoter of the cholorophyll a-b binding protein. These two promoters are known to be light-induced, in eukaryotic plant cells (see, for example, *Genetic Engineering of Plants, An Agricultural Perspective,* A. Cashmore, Pelham, N.Y., 1983, pp. 29–38, G. Coruzzi et al., *J. Biol. Chem.,* 258:1399 (1983), and P. Dunsmuir, et al., *J. Molecular and App. Gen.,* 2:285 (1983)).

The expression cassette comprising the structural gene for CMIII operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention. Since these hosts are also microorganisms, it will be essential to ensure that plant promoters which do not cause expression of the CMIII in bacteria are used in the vector.

The isolated cloning vector will then be introduced into the plant cell using any convenient technique, including electroporation (in protoplasts), retroviruses, bombardment, and microinjection, into cells from monocotyledonous or dicotyledonous plants, in cell or tissue culture, to provide transformed plant cells containing as foreign DNA at least one copy of the DNA sequence of the plant expression cassette. Preferably, the monocotyledonous species will be selected from maize, sorghum, wheat and rice, and the dicotyledonous species will be selected from soybean, alfalfa, tobacco and tomato. Using known techniques, protoplasts can be regenerated and cell or tissue culture can be regenerated to form whole fertile plants which carry and express the gene for CMIII. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to diseases caused by microorganisms selected from *Fusarium graminearum, Fusarium moniliforme, Aspergillus flavus, Alternaria longipes, Sclerotinia sclerotiorum,* and *Sclerotinia trifoliorum* to plants of a susceptible taxon, comprising the steps of:

a) culturing cells or tissues from at least one plant from the taxon, b) introducing into the cells of the cell or tissue culture at least one copy of an expression cassette comprising a structural gene for CMIII, operably linked to plant regulatory sequences which cause the expression of the CMIII structural gene in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the CMIII structural gene and associated regulatory sequences via crossing and backcrossing. Such intermediate methods will comprise the further steps of a) sexually crossing the disease-resistant plant with a plant from the disease-susceptible taxon;

b) recovering reproductive material from the progeny of the cross; and c) growing disease-resistant plants from the reproductive material. Where desirable or necessary, the agronomic characteristics of the susceptible taxon can be substantially preserved by expanding this method to include the further steps of repetitively:

a) backcrossing the disease-resistant progeny with disease-susceptible plants from the susceptible taxon; and b) selecting for expression of antimicrobial activity (or an associated marker gene) among the progeny of the backcross, until the desired percentage of the characteristics of the susceptible taxon are present in the progeny along with the gene imparting antimicrobial activity.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens,* which can then be used to transfer the vector into susceptible plant cells, primarily from dicotyledonous species. Thus, this invention provides a method for imparting antimicrobial activity and disease resistance in *Agrobacterium tumefaciens*-susceptible dicotyledonous plants in which the expression cassette is introduced into the cells by infecting the cells with *Agrobacterium tumefaciens,* a plasmid of which has been modified to include a plant expression cassette of this invention.

The following description further exemplifies the compositions of this invention and the methods of making and using them. However, it will be understood that other methods, known by those of ordinary skill in the art to be equivalent, can also be employed.

INDUSTRIAL APPLICABILITY

Example 1

Purification of CMIII.

CMIII was obtained from two sources, the public corn variety B73 and proprietary corn variety MH18 as follows:

Ground maize seeds were extracted at room temperature with 0.1 N $H_2SO_4$. The resulting extract was neutralized and centrifuged to remove insoluble material. The extract was adjusted to pH 5.2 and chromatographed on a carboxymethyl cellulose cation exchange column equilibrated in 0.3 M ammonium acetate, eluting with a gradient of ammonium acetate of from 0.4 to 1.0 M. (FIG. 1). CMIII eluted at approximately 0.8 M in a series of A280 peaks that also includes other peptides of similar size and properties.

CMIII can also be purified by chromatography on a Mono-S cation exchange FPLC column (Pharmacia) with a similar gradient of ammonium acetate. Peak MS-16 corresponds to CMIII in FIG. 2.

CMIII elutes as a single major UV-absorbing peak from a reverse phase HPLC column ($C_{18}$, equilibrated in 0.1% TFA; 10–40% gradient of acetonitrile/0.1% TFA), indicating that it is substantially free of contaminating proteins or peptides.

Example 2

Characterization of CMIII

CMIII migrated as a single coomassie blue-staining band in both SDS-urea and SDS-TRIS-Tricine polyacrylamide gel systems, with a relative mobility indicating a molecular weight of 4000 daltons. Amino acid analysis showed a high proportion of arginine (10 residues/mole), glutamate/glutamine (7 residues/mole) and cysteine (4 residues/mole).

Tryptophan, which is not detected by amino acid analysis, was detected (approx. 1 residue/mole) by quantitative oxidation with N-bromosuccinimide. Circular dichroism spectroscopy indicates a high alpha-helical content.

The first 24 N-terminal amino acids of CMIII were identified by sequencing of peptide blotted from TRIS-Tricine SDS-PAGE gels to Immobilon P polyvinylidine fluoride membranes. In addition, five endo-Gluc-C fragments of CMIII were purified by reverse phase HPLC and sequenced, confirming and tentatively extending the peptide sequence to a total of 34 residues, for a total molecular weight of approximately 3900 daltons. In this way, CMIII was found to have the sequence (SEQ ID No:1) Arg-Ser-Gly-Arg-Gly-Glu-Cys-Arg-Arg-Gln-Cys-Leu- Arg-Arg-His-Glu-Gly-Gln-Pro-Trp-Glu-Thr-Gln-Glu-Cys-Met-Arg-Arg-Cys-Arg-Arg-Arg-Gly-Gly.

From this analysis, it can be seen that CMIII is structurally different from any of the monocot thionins, which unlike CMIII are high in lysine and low in arginine. CMIII is surprisingly similar to a mammalian antimicrobial peptide, defensin NP1 from rabbits, although CMIII is much higher in glutamate and has 4 rather than 6 cysteines. There is slight similarity to a basic peptide obtained from pumpkin seeds (Naisbitt et al., Plant Physiol. 1988, 88:770) which is high in arginine and glutamate/glutamine but which lacks cysteine.

CMIII was further characterized by its CD, UV-absorption and flourescence spectra, as illustrated in FIGS. 4, 5 & 6.

Example 3

Identification of the CMIII gene and insertion into bacteria

The amino acid sequence of CMIII includes several stretches that are amenable to construction of synthetic, degenerate oligonucleotide probes; one example is residues 20–26 (Try-Glu-Thr-Gln-Glu-Cys-Met-Arg), which is coded by the nucleotide sequence TGG GAR ACN CAR GAR TGY ATG MG, where Y=T or C, R=A or G, M=A or C, and N=A or G or T or C. Another, overlapping stretch is residues 15–21 (His-Glu-Gly-Gln-Pro-Tryp-Glu-Thr), which can be coded for by the following: CAY GAR GGN CAR CCN TGG GAR AC. These oligonucleotides are end-labelled with $^{32}$P and used to screen a maize genomic or cDNA library. Clones which hybridize to both probes are subcloned into an appropriate single-stranded phage vector such as Bluescript KS+, restriction sites in the cloned DNA are mapped, and the region corresponding to the CMIII gene identified by Southern hybridization of restriction fragments using the oligonucleotides as probes. The CMIII gene region is subcloned and sequenced to verify identity and determine the open reading frame for protein synthesis. Finally, restriction sites are engineered at either end of the open reading frame by site-directed mutagenesis, to allow the gene to be introduced into a plant expression cassette.

Alternatively, of course, a complete synthetic gene can be constructed from the sequence given herein for the CMIII protein.

Example 4

Expression of the CMIII Gene in Plants

Figure 7:
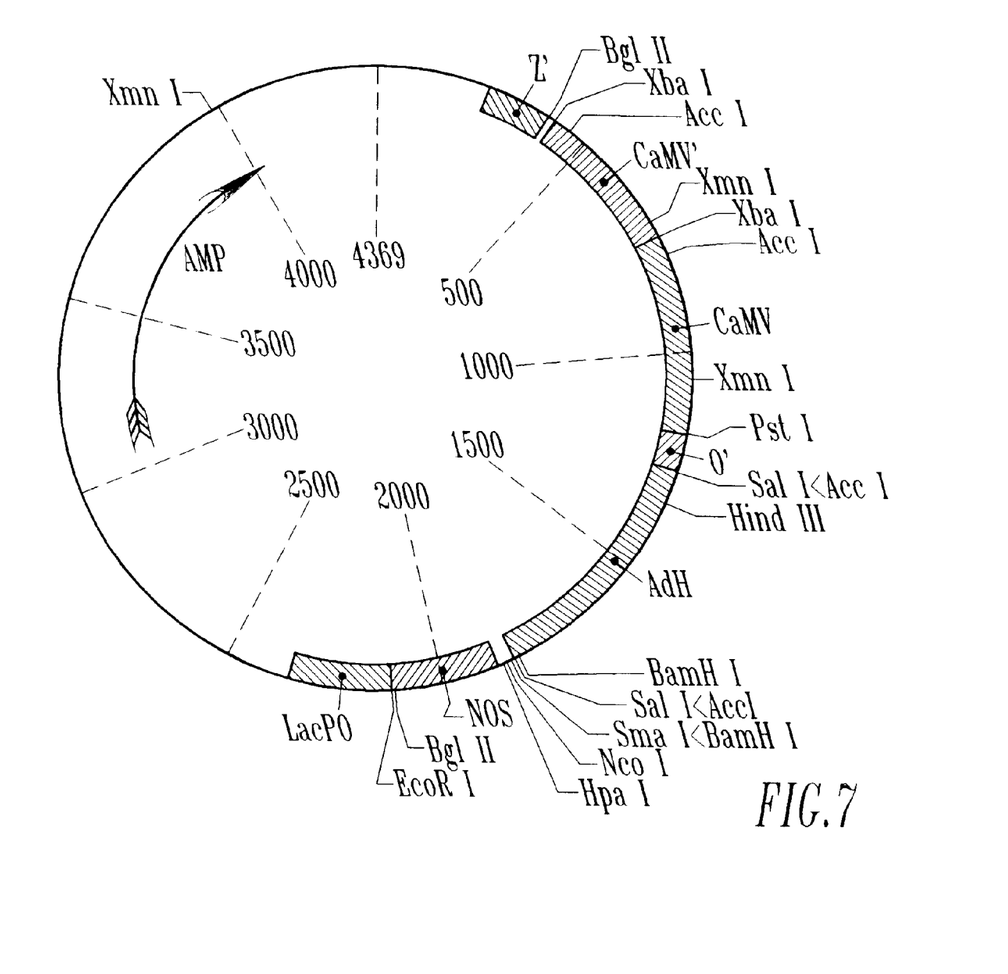
FIGS. 7–8 is a plasmid map of plasmid pPHI412.

A plant expression cassette, employing the regulatory sequences developed by Beach, et al., and containing the CMIII gene, is constructed. The restriction map of the preferred plasmid, designated pPHI414, is illustrated in FIG. 7. This plasmid contains an enhanced 35S promoter spanning nucleotides −421 to +2 of Cauliflower Mosaic Virus with the region from −421 to −90 duplicated in tandem, a 79 bp HindIII SalI fragment from pJII101 spanning the 5' leader sequence of Tobacco Mosaic Virus, a 579 bp fragment spanning the first intron from maize AdH1-S, and a 281 bp fragment spanning the polyadenylation site from the nopaline synthase gene in pTiT37.

Figure 8:
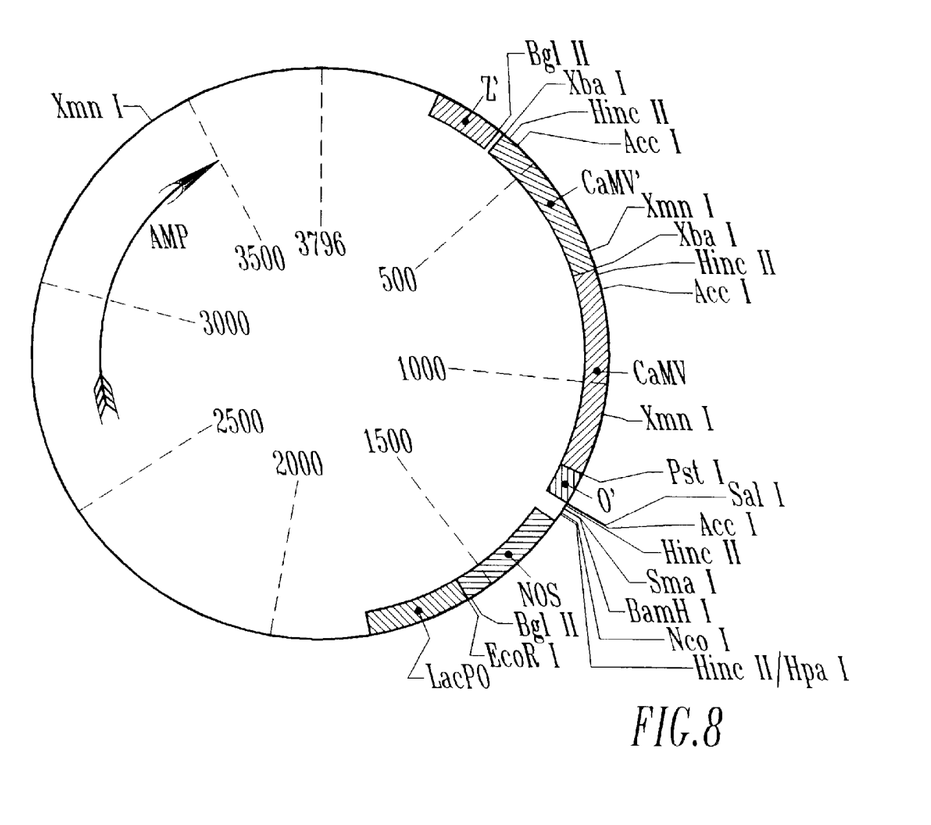

Another construct which can be used as an expression cassette is the pPHI412 plasmid shown in FIG. 8. It differs from pPHI414 in that it lacks the AdH intron segment. However, like pPHI414, it is constructed to have numerous restriction sites between the O' segment and the NOS segment, which sites can be conveniently used for splicing the CMIII structural gene into position.

This vector can be cotransformed with a similar plasmid containing a selectable marker for antibiotic resistance into Black Mexican Sweet corn protoplasts by electroporation. These protoplasts can then be induced to regenerate cell walls and develop into callus by conventional techniques. Likewise, this callus can then be subjected to antibiotic selection to select for transformed colonies, and these colonies can be tested for expression of CMIII with antisera for the appropriate CMIII using known methods. The efficiency of protection can be measured by infesting callus (or suspension cultures derived from callus) with the target microorganism and measuring survival percentages.

The CMIII gene can be introduced into embryogenic maize callus by methods similar to those used for Black Mexican Sweet. Embryogenic callus can be regenerated to whole fertile plants. The antimicrobial activity and disease resistance imparted by the endogenous production of the CMIII is a simply inherited, dominant trait and can, if desired, be introduced into other plant varieties of the species by simple crossing or backcrossing.

As used herein, the term "antimicrobial amount" means at least an $LD_{50}$ of the CMIII as measured against a target organism.

Example 5

Microorganism Susceptibility to CMIII

In spore germination and hyphal growth assays against plant pathogenic fungi, CMIII has been found to have inhibitory activity against *Fusarium graminearum, Sclerotinia sclerotiorum,* and *Sclerotinia trifoliorum* at a concentration of 112 µg/mL. Other fungi, including *Fusarium moniliforme* and *Aspergillus flavus,* were slightly inhibited at the concentration. CMIII activity is reduced substantially in the presence of plant cell extracts.

Figure 1:
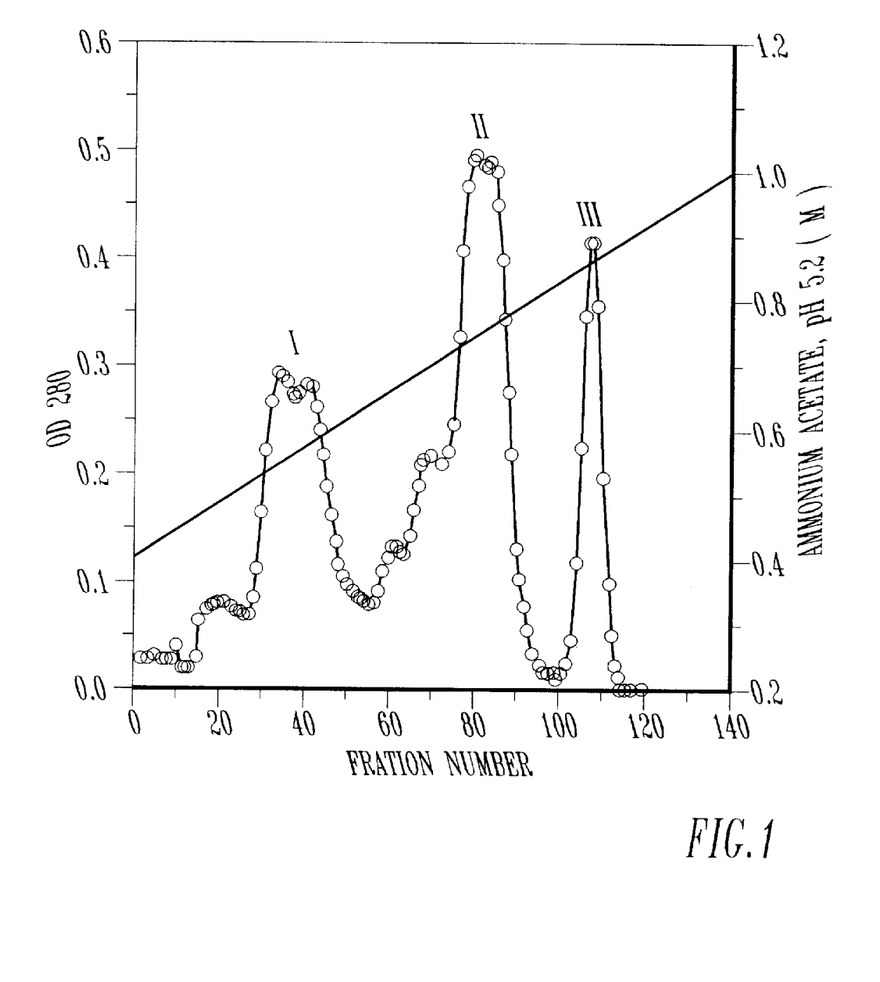
FIG. 1 is a graph showing the results of cellulose chromatography of crude plant extract as described in the examples 1 & 2.
Figure 2:
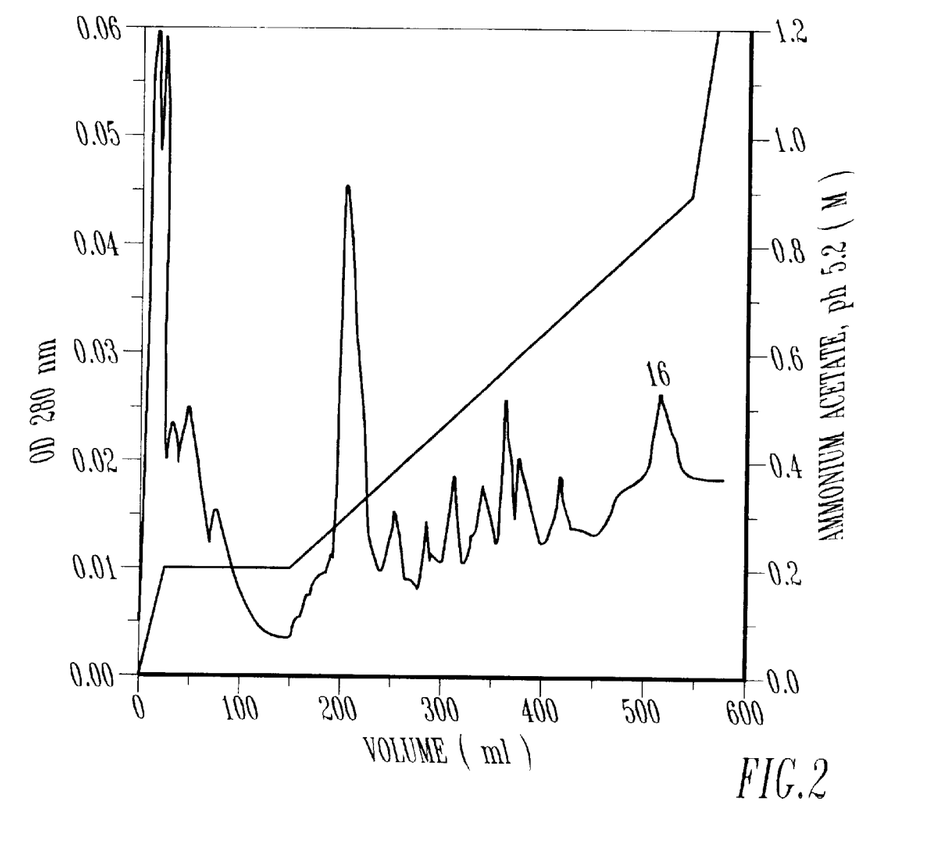
FIG. 2 is a graph illustrating the results of FPLC purification of crude plant extract as described in Examples 1 & 2.
Figure 3:
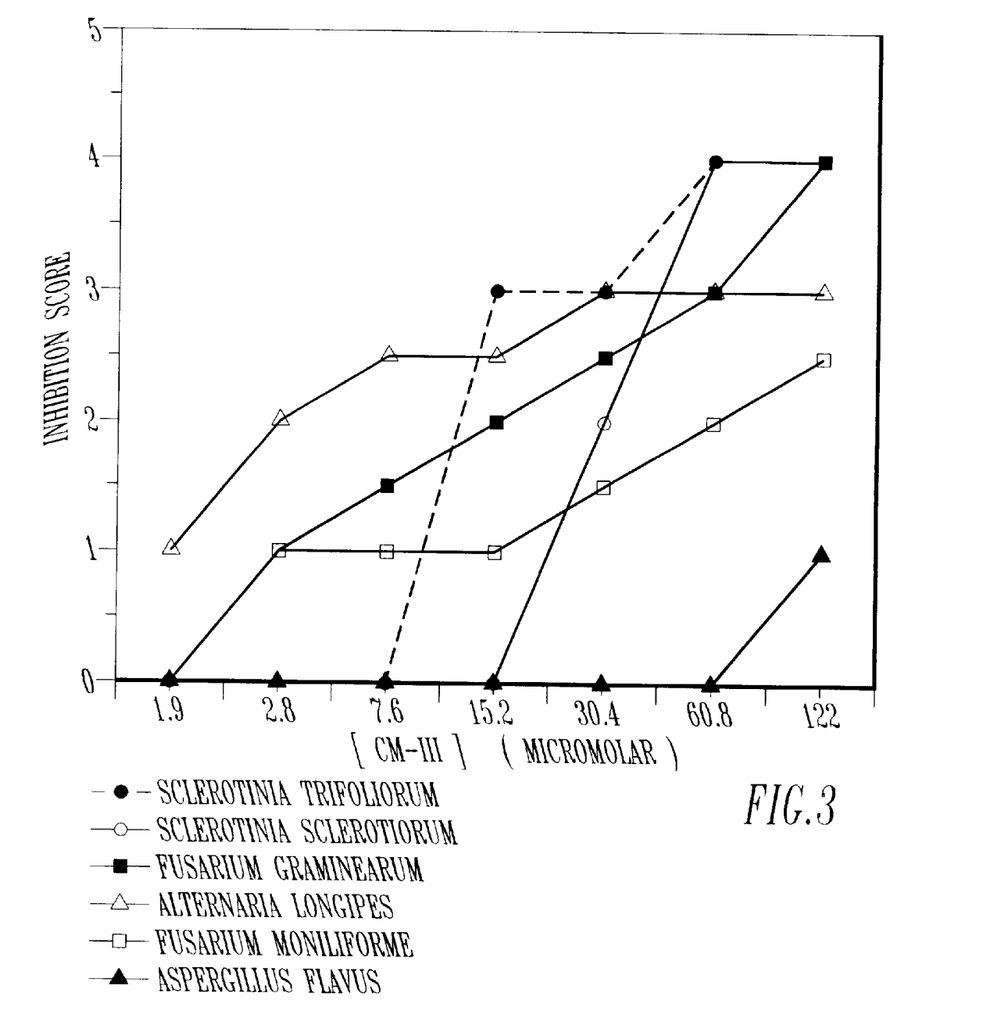
FIG. 3 is a graph illustrating the data from a single microbial inhibitation experiment. Inhibition was scored relative to control wells containing no peptide, as described in Example 5.

Approximately 150 conidia or approximately 5 to 20 mycelial fragments were incubated in 90 microliters of culture medium in microtiter plate wells. The culture medium was a broth medium containing 0.25% yeast extract, 0.1% casein hydrolyzate, 1% glucose, 0.025% calcium nitrate, 0.005% potassium phosphate, and 0.00625% magnesium sulfate. The peptide at the test concentration was added in 10 microliters in water or buffer, and the plates were incubated from 1 to three days at 28 degrees C. At the end of the incubation period, the wells were examined and mycelial growth was scored versus control wells as follows:

0=No inhibition
1=Slight Inhibition
2=Moderate Inhibition
3=Almost Complete Inhibition
4=Complete Inhibition results of one such study are indicated in FIG. 3.

In other studies, *Alternaria longipes* was found to be the most sensitive of the fungi to the action of CMIII, showing noticeable inhibition at 1.9 micromolar. *Aspergillus flavus* was the most resistant, showing slight inhibition at 122 micromolar. The maize seed pathogens *Fusarium graminearum* and *Fusarium moniliforme* were noticeably inhibited down to 3.8 micromolar, although *F. moniliforme* was not completely inhibited even at 122 micromolar. Sclerotinia isolates were inhibited strongly at higher concentrations, but inhibition was not observed at lower concentrations (below 30.4 micromolar for *S. sclerotiorum,* and below 15.2 micromolar for *S. trifoliorum.*)

In yet another study *A. longipes* was not affected by CMIII at 3 µM.

In summary, CMIII is inhibitory to a wide range of plant pathogens, although inhibition profiles vary widely from pathogen to pathogen.

What is claimed is:

1. An isolated CMIII peptide having the sequence of SEQ. ID. NO. 1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 34 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:1:

Arg Ser Gly Arg Gly Glu Cys Arg Arg Gln Cys Leu Arg Arg His Glu
   1               5                   10                  15

Gly Gln Pro Trp Glu Thr Gln Glu Cys Met Arg Arg Cys Arg Arg Arg
                   20                  25                  30

Gly Gly (2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

TGGGARACNC ARGARTGYAT GMG                                          23

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

CAYGARGGNC ARCCNTGGGA RAC                                          23